United States Patent [19]

Kanemoto et al.

[11] Patent Number: 5,690,104
[45] Date of Patent: Nov. 25, 1997

[54] APPARATUS AND METHOD FOR MEASURING OXYGEN SATURATION IN BLOOD AND APPARATUS AND METHOD FOR MEASURING CONCENTRATION OF LIGHT-ABSORBING MATERIALS IN BLOOD

[75] Inventors: Michio Kanemoto; Naoki Kobayashi; Takuo Aoyagi, all of Tokyo, Japan

[73] Assignee: Nihon Kohden Corporation, Tokyo, Japan

[21] Appl. No.: 661,169

[22] Filed: Jun. 10, 1996

Related U.S. Application Data

[62] Division of Ser. No. 458,656, Jun. 2, 1995.

[30] Foreign Application Priority Data

Jun. 2, 1994 [JP] Japan ................................. 6-121346

[51] Int. Cl.⁶ .................................................. A61B 5/00
[52] U.S. Cl. ............................................ 128/633; 128/666
[58] Field of Search ............................... 128/633, 664, 128/665, 666; 356/39, 41

[56] References Cited

U.S. PATENT DOCUMENTS

| | | | |
|---|---|---|---|
| 3,677,648 | 7/1972 | Dorsch | 128/666 |
| 4,167,331 | 9/1979 | Nielsen | 128/633 |
| 5,154,176 | 10/1992 | Kanda . | |
| 5,178,141 | 1/1993 | Kanda | 128/633 |
| 5,351,685 | 10/1994 | Potratz | 128/633 |
| 5,385,143 | 1/1995 | Aoyagi | 128/633 |
| 5,458,128 | 10/1995 | Polanyi et al. | 128/633 |
| 5,494,031 | 2/1996 | Hoeft | 128/633 |
| 5,503,148 | 4/1996 | Pologe et al. | 128/633 |

*Primary Examiner*—Jennifer Bahr
*Assistant Examiner*—Eric F. Winakur
*Attorney, Agent, or Firm*—Sughrue, Mion, Zinn, Macpeak & Seas, PLLC

[57] ABSTRACT

Intensities of light of two different wavelengths transmitted through a tissue of a living body are measured during a first time period. A data processor determines a first regression line using logarithmically processed data corresponding to the light intensities measured during the first time period. An operator injects a dye into the living body and measurements of intensities of light at the two different wavelengths are made during a later time period. The data processor determines a second regression line using logarithmically processed data corresponding to the light intensities measured during the later time period. The data processor finds an intersection of the two regression lines and uses the intersection to determine a bloodless level point. The processor then forms a dye dilution curve incorporating the bloodless level point data.

4 Claims, 8 Drawing Sheets

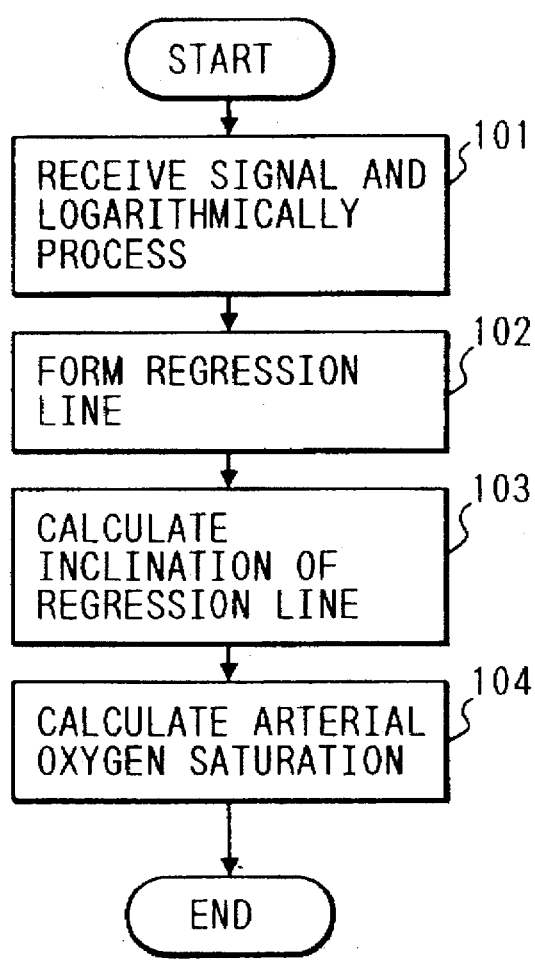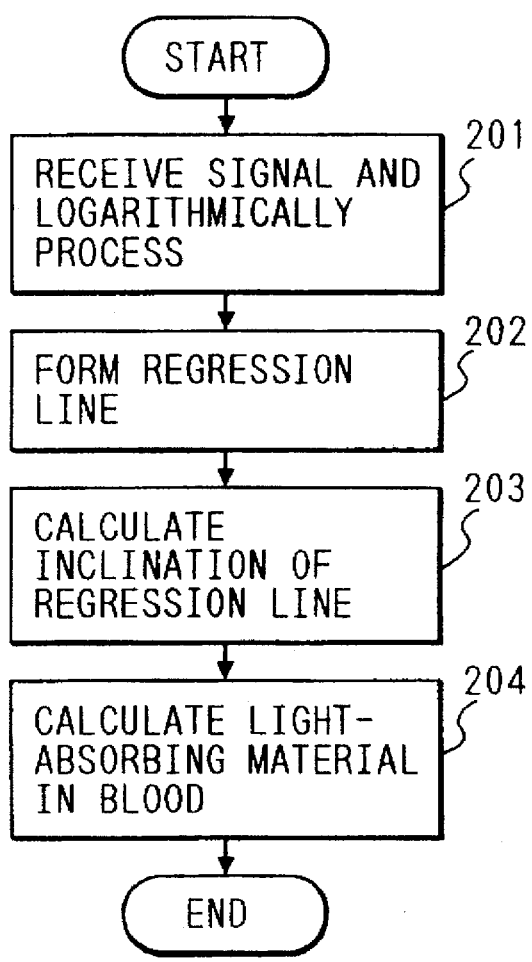

APPARATUS AND METHOD FOR MEASURING OXYGEN SATURATION IN BLOOD AND APPARATUS AND METHOD FOR MEASURING CONCENTRATION OF LIGHT-ABSORBING MATERIALS IN BLOOD

This is a divisional of application Ser. No. 08/458,656 filed Jun. 2, 1995.

BACKGROUND OF THE INVENTION

1. Field of the Invention

The present invention relates to the improvement of an apparatus for measuring oxygen saturation in blood and an apparatus for measuring the concentration of light-absorbing materials in blood, which are used for diagnosis of the circulating system in the medical field.

2. Related Art

Typical examples of this type of apparatus, which simplifies the measurement with lessened invasion, are a pulse oximeter and an apparatus for measuring the concentration of light-absorbing materials in blood, which is based on the pulse oximeter.

In the pulse oximeter, light of different wavelengths are transmitted through a living body. Light transmitted through a tissue of the living body is measured. Assumption that a pulsation of the tissue transmitted light is due to a variation of the effective thickness of an arterial blood is made. Concentration ratios of a plurality of in-blood light absorbing materials are calculated on the basis of the fact that an amplitude of the pulsation varies depending on the wavelength thereof.

The principle of the pulse oximeter needs recognition of the amplitude information of the pulsation; viz., the maximum value or peak value and the minimum value or the bottom value of the pulsation, in determining the concentration ratios of the light absorbing materials in blood. Where the amount of distal blood is caused to change by body motion or organic factors, it is very difficult to recognize the peak value and the bottom value of the pulsation. This leads to degradation of the measuring accuracy.

In continuously measuring the dye concentration in blood non-invasively on the basis of the principle of the pulse oximeter, a ratio of the concentration of hemoglobin and the concentration of dye in blood is determined. The concentration ratio is combined with the concentration of hemoglobin in the blood, which is determined in another measurement, to thereby obtain the concentration of dye in blood.

As described above, the pulse oximeter computes the concentration of light-absorbing materials in blood on the basis of the amplitude information of the pulsation. The dye concentration rapidly varies in an initial circulatory part in a dye dilution curve, it is not allowed to smooth the dye concentration obtained. Where the circulatory condition of a patient whose dye dilution curve is to be formed is bad and the amplitude of the pulsation is small, the values of the concentration of dye in blood measured every pulsation wave are poor in reliability, and a configuration of the dye dilution curve is irregular.

One of the possible ways to solve the above problem is to use the whole information on a pulsation signal which includes the amplitude of the pulsation.

An intensity of transmitted light which would be gained if no blood is present in the tissue is referred to as a bloodless level.

This bloodless level can be calculated using a pulsation of the light transmitted through the tissue. An optical density of the blood is obtained from the bloodless level and actual tissue-transmitted light, and a dye dilution curve is obtained from time variations of the optical densities of the blood by two wavelengths. This method is already disclosed (e.g., Published Unexamined Japanese Patent Application No. Sho. 63-165757).

In the conventional pulse oximeter or the apparatus for measuring the concentration of light-absorbing materials in blood, the data used consists of the peak value and the bottom value of a pulsation of tissue transmitted light.

The reliability of the values of the data is poor where the amplitude of the pulsation is small, as described above. To recognize the peak value and the bottom value, a short sampling interval of the pulsation signal is required, so that great power is consumed to light up the light generating means, such as an LED.

To obtain the bloodless level, signals representative of intensities of the tissue transmitted light at two time points before and after a dye dilution curve appears are required.

A speed of a variation of the concentration of dye in the blood must be satisfactorily stable at a time point after the dye dilution curve appears. When a reasonable point is previously determined, it is inevitably a time point where it is satisfactorily slow.

Accordingly, the in-blood dye concentration is very low, and a measurement accuracy of the bloodless level is poor.

SUMMARY OF THE INVENTION

For the above background reasons an object of, the present invention is to provide an apparatus for measuring oxygen saturation in blood and an apparatus for measuring the concentration of light-absorbing materials in blood, which are high in measuring accuracy and low in power consumption.

According to an aspect of the present invention, there is provided an apparatus for measuring oxygen saturation in blood comprising: light generating means for projecting light beams of two different wavelengths to a living body; photo sensing means for receiving light beams transmitted through the living body and converting the received light beams into electrical signals; regression line computing means for forming a regression line, using the values of the two output signals of the photo sensing means at a plurality of time points, where the coordinates of the ordinate and the abscissa represent the magnitudes of the output signals; inclination computing means for computing an inclination of the regression line formed by said regression line computing means; and oxygen saturation computing means for computing an oxygen saturation using the inclination obtained by said inclination computing means.

According to another aspect of the present invention, there is provided an apparatus for measuring the concentration of light-absorbing materials in blood comprising: light generating means for projecting light beams of two different wavelengths to a living body; photo sensing means for receiving light beams transmitted through the living body and converting the received light beams into electrical signals; regression line computing means for forming a regression line, using the values of the two output signals of the photo sensing means at a plurality of time points, on the coordinates of which the ordinate and the abscissa represent the magnitudes of the output signals; inclination computing means for computing an inclination of the regression line formed by said regression line computing means; and in-blood light-absorbing material concentration computing means for computing the concentration of light absorbing materials in blood using the inclination obtained by said inclination computing means.

According to another aspect of the present invention, there is provided an apparatus for measuring the concentration of light-absorbing materials in blood comprising: light generating means for projecting light beams of two different wavelengths to a living body; photo sensing means for receiving light beams transmitted through the living body and converting the received light beams into electrical signals; regression line computing means for forming regression lines for at least two periods, using the values of the two output signals of the photo sensing means at a plurality of time points, where the coordinates of the ordinate and the abscissa represent the magnitudes of the output signals; bloodless level computing means for computing a bloodless level of the light beams transmitted through the living body by using the intersections of the extensions of at least two regression lines obtained by said regression line computing means; absorbance computing means for computing a blood absorbance of the transmitted light beams of the different wavelengths by using the bloodless level calculated by said bloodless level computing means and the output signals of said photo sensing means; and concentration computing means for computing the concentration of light absorbing materials in blood using the absorbance calculated by said bloodless level computing means.

According to another aspect of the present invention, there is provided an apparatus for measuring the concentration of light-absorbing materials in blood is characterized in that said bloodless level computing means operates such that said bloodless level computing means successively obtains intersections of a regression line during a period where a dye concentration in blood is zero before a dye dilution curve appears and regression lines during plural periods after a dye dilution curve appears, and when a dispersion of the intersections falls within a predetermined range, said bloodless level computing means determines that the center of the distribution of intersections is a bloodless level.

According to the present invention, where an oxygen saturation is constant during the measurement, one regression line is formed.

An inclination of the regression line is exactly expressed by a ratio of absorbances of transmitted light beams of two wavelengths. As a result, an accurate oxygen saturation is secured.

According to the present invention, where the concentration of light absorbing materials in blood is constant during the measurement, one regression line is formed.

An inclination of the regression line is exactly expressed by a ratio of absorbances of transmitted light beams of two wavelengths. As a result, an accurate light-absorbing material concentration is secured, and a fewer number of sampling operations for forming the regression line are required. These facts enable the lighting frequency the of LED in the light generating means to be reduced, and further to reduced power consumption.

According to the present invention, a bloodless level may be calculated using the overall pulsation. When the concentration of light absorbing materials in blood is measured on the basis of this method, the measurement result is exact.

According to the present invention, the intersection is obtained every time the regression line is formed. When a dispersion of the intersections is within a predetermined range, the center of the distribution of intersections is determined to be a bloodless level. Accordingly, time taken till the bloodless level is obtained is reduced.

BRIEF DESCRIPTION OF THE DRAWINGS

FIG. 3 is a flowchart useful in explaining the operation of the first embodiment of the present invention;

FIG. 6 is a flowchart useful in explaining the operation of the second embodiment of the present invention;

DETAILED DESCRIPTION OF THE PREFERRED EMBODIMENTS

Figure 1:
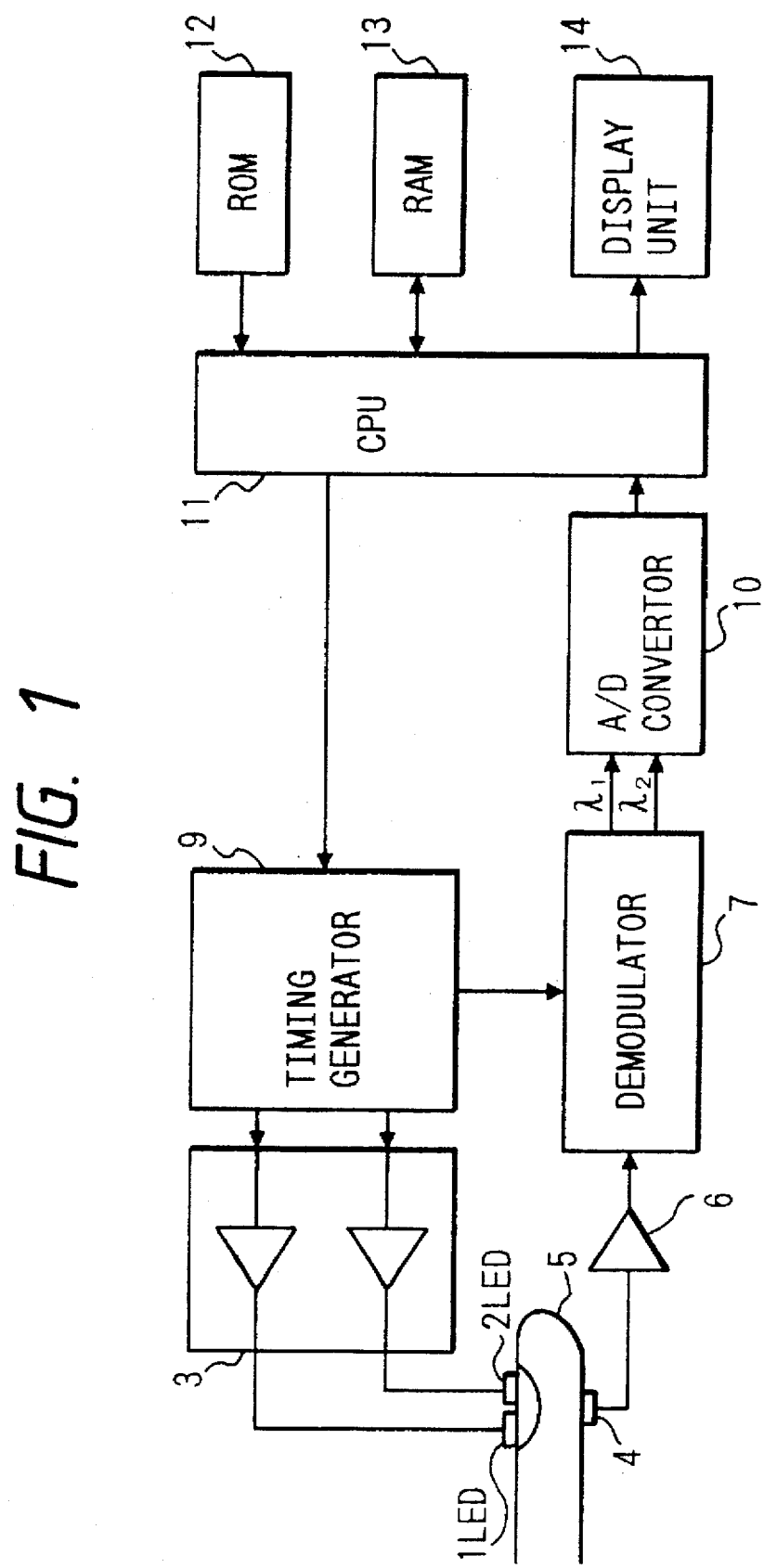
FIG. 1 is a block diagram showing an overall arrangement of a first embodiment of the present invention.

Preferred embodiment will now be described with references to the accompanying the drawings.

FIRST EMBODIMENT

The first embodiment of the invention will be described.

In this embodiment, the present invention is applied to the form of an apparatus for measuring oxygen saturation in blood. The principle of this embodiment will first be described.

An absorbance A of light transmitted through a tissue can be expressed by the following equation, which is constructed on the basis of Arthur Schuster's theory and experiments $$A = Ab + Aa = \ln I - \ln I in \quad (1)$$
$$= \{Eh(Eh + F)\}^{1/2} \cdot Hb \cdot D + Aa$$

where Ab: absorbance of the blood

Aa: absorbance of other tissues

I: intensity of transmitted light

Iin: intensity of incident light

Eh: light absorbing coefficient of hemoglobin

F: a scattering coefficient of the blood

Hb: hemoglobin concentration in the blood

D: thickness of the blood

When the thickness of the blood is incremented to D+ΔD by a pulsation of blood, the equation (1) is rewritten as $$A+\Delta Ab = \ln I - \Delta \ln I - \ln I in = \{Eh(Eh+F)\}^{1/2} \cdot Hb \cdot (D+\Delta D) + Aa \quad (2)$$

Equation (2)–the equation (1):

$$\Delta Ab = -\Delta \ln I = \{Eh(Eh+F)\}^{1/2} \cdot Hb \cdot \Delta D \quad (3)$$

For wavelengths λ1 and λ2, equation (3) can be rewritten into $$\Delta Ab1 = -\Delta \ln I1 = \{Eh1(Eh1+F)\}^{1/2} \cdot Hb \cdot \Delta D \qquad (4)$$

$$\Delta Ab2 = -\Delta \ln I2 = \{Eh2(Eh2+F)\}^{1/2} \cdot Hb \cdot \Delta D \qquad (5)$$

In equations (4) and (5), suffixes 1 and 2 indicate those for the wavelengths λ1 and λ2.

If the equation (4)÷equation (5)=Φ12, then we have $$\Phi 12 = \Delta Ab1/\Delta Ab2 = \Delta \ln I1/\Delta \ln I2 = \{Eh1(Eh1+F)\}^{1/2}/\{Eh2(Eh2+F)\}^{1/2} \quad (6)$$

Eh1 and Eh2 are given by $$Eh1 = SEo1 + (1-S)Er1 \qquad (7)$$

$$Eh2 = SEo2 + (1-S)Er2 \qquad (8)$$

where S: oxygen saturation

Eo1, Eo2: light absorbing coefficient of oxyhemoglobin at the wavelengths λ1 and λ2.

Er1, Er2: light absorbing coefficient of deoxyhemoglobin at the wavelengths λ1 and λ2.

Figure 2:
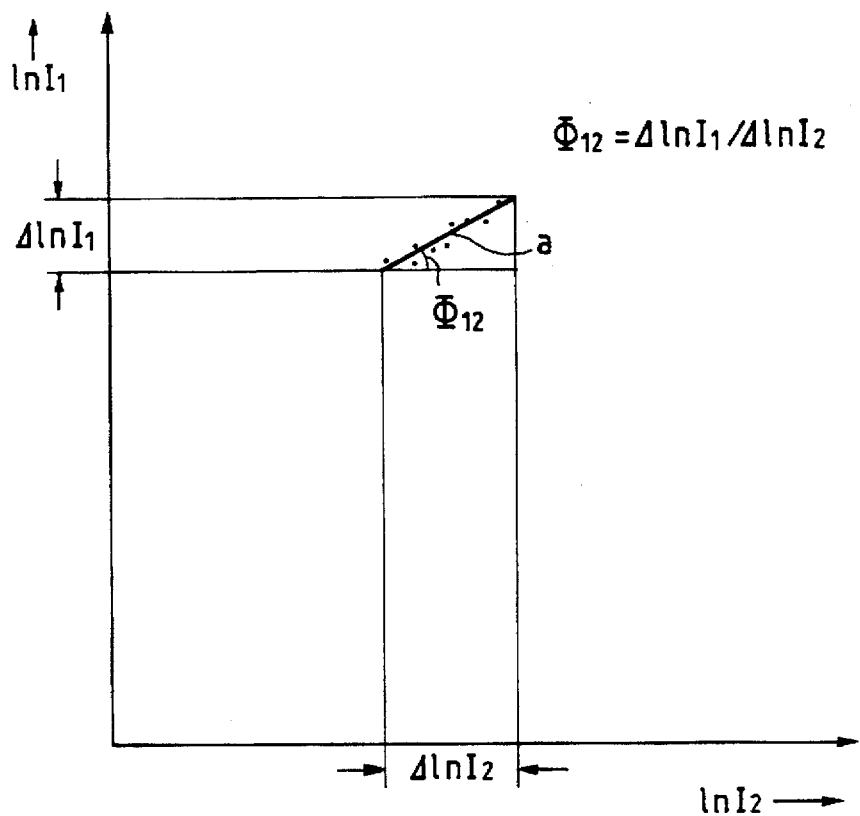
FIG. 2 is a graph useful in explaining the operation of the first embodiment of the present invention.

In the equations (6) to (8), F, Eo1, Eo2, Er1, and Er2 are known. Accordingly, the oxygen saturation S can be calculated by measuring ΔlnI1 and ΔlnI2 and obtaining Φ.

lnI2 and lnI1 were measured at given time intervals, and the results were plotted on a graph of FIG. 2 where the abscissa represents lnI2 and the ordinate lnI1. These points are processed by the method of least squares, to thereby form a regression line a. If the oxygen saturation S is fixed, a point obtained by the measurement goes and returns along the regression line every one pulsation. An inclination of the regression line is given by ΔlnI1/ΔlnI2. Then, the oxygen saturation S can be obtained when the equations (6) to (8) are calculated using the inclination Of the regression line.

A specific example of the apparatus for measuring oxygen saturation in blood, designed on the basis of the abovementioned principle, will be described.

FIG. 1 is a block diagram showing an overall arrangement of an apparatus for measuring oxygen saturation in blood according to a first embodiment of the present invention. LED1 is an element for generating light of the wavelength λ1, and LED2 is an element for generating light of the wavelength λ2. A driver circuit 3 is a circuit for driving these LED1 and LED2. Light beams are emitted from LED1 and LED2, and transmitted through a living body 5. A photo diode 4 is disposed so as to receive the light beams transmitted through the living body. The photo diode 4 produces electric signals varying in accordance with intensities of the transmitted light beams. The signals from the photo diode 4 are amplified by an amplifier 6, and demodulated by a demodulator 7. A timing generator 9 sends timing signals to the driver circuit 3 and the demodulator 7. As a result, the LED1 and the LED2 are driven to emit light beams at given timings and the demodulator 7 demodulates the received electrical signals to produce signals of the wavelength λ1 and the wavelength λ2 at timings associated with the former timings. An A/D converter 10 converts the analog signals from the demodulator 7 into digital signals, which in turn are applied to a CPU 11.

The CPU 11 writes necessary data into a RAM 13 using the received digital signals and the programs and data stored in a ROM 12. The CPU 11 reads the data out of the memory, and carries out a computing process of the readout data, and outputs the results of the Computing process to a display device 14 or a recorder (not shown). A program as described in a flowchart shown in FIG. 3 is stored in the ROM 12.

The operation of the apparatus for measuring oxygen saturation in blood thus constructed will be described with reference to the flowchart.

The CPU 11 receives the signals containing the intensities I1 and I2 of the transmitted light beams, which are produced at given time intervals by the A/D converter 10. The CPU 11 converts these received signals into signals that are logarithmically processed (step 101).

In this case, the light intensities I1 and I2 are collected at least at two points (including peak and bottom points) on each of a plurality of pulsations. The CPU 11 plots the data that were stored in step 101 an a graph where the coordinates of the abscissa represents lnI2 and the ordinate represents lnI1, and applies the method of least squares to those plotted data, to thereby form a regression line (step 102). The CPU 11 computes an inclination of the regression line (step 103), and computes an oxygen saturation S by using the equations (6) to (8) (step 104). The results of the computing process are displayed on the screen of the display device 14 or recorded by a recorder (not shown).

As described above, the apparatus for measuring oxygen saturation in blood thus constructed and operated measures the intensities lnI1 and lnI2 of the transmitted light on at least two pulsations. Therefore, the apparatus can exactly determine the oxygen saturation S.

SECOND EMBODIMENT

The second embodiment of the invention will be described.

In this embodiment, the present invention is applied to the form of an apparatus for measuring the concentration of light-absorbing materials in blood. The principle of the this embodiment will first be described.

Where blood contains hemoglobin and another light-absorbing material, the following equation holds:

$$\Phi 34 = \Delta \ln I3/\Delta \ln I4 \qquad (9)$$
$$= \{(Eh3 + Ed3Cd/Hb)(Eh3 + Ed3Cd/Hb + F)\}^{1/2}/$$
$$\{(Eh4 + Ed4Cd/Hb)(Eh4 + Ed4Cd/Hb + F)\}^{1/2}$$

where Ed: light absorbing coefficient of the additional light absorbing material;

Cd: concentration of the additional light absorbing material.

This equation can be obtained in a manner that is similar to the manner in which the equation (6) is lead from the equation (1), assuming that $Ab=\{(Eh+EdCd/Hb)(Eh+EdCd/Hb+F)\}^{1/2} \cdot Hb \cdot D$. Eh, Hb, F and D are the same as those already referred to. suffixes 3 and 4 indicate those for the wavelengths λ3 and λ4.

Eh3 and Eh4 are given by $$Eh3 = SEo3 + (1-S)Er3 \qquad (10)$$

$$Eh4 = SEo4 + (1-S)Er4 \qquad (11)$$

In the above equations, Eo indicates a light absorbing coefficient of oxyhemoglobin, and Er indicates a light absorbing coefficient of deoxyhemoglobin, as already described.

Assuming that the light absorbing coefficient Ed4 of a light absorbing material is zero at the wavelength λ4, the equation (9) can be rewritten into $$\Phi 34 = \Delta \ln I3/\Delta \ln I4 \qquad (12)$$
$$= \{(Eh3 + Ed3Cd/Hb)(Eh3 + Ed3Cd/Hb + F)\}^{1/2}/$$
$$\{Eh4(Eh4 + F)\}^{1/2}$$

Figure 4:
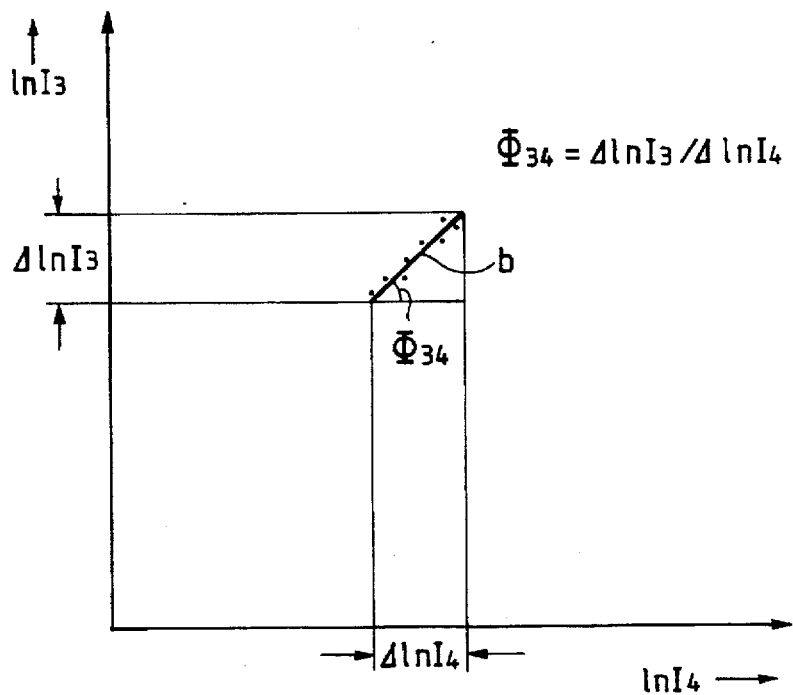
FIG. 4 is a graph useful in explaining the operation of a second embodiment of the present invention.

In the case of the blood in which the oxygen saturation S and the hemoglobin concentration Hb are already measured, other factors than Cd are known in the equation (12). In this case, Cd can be obtained by measuring $\Delta \ln I3$ and/$\Delta \ln I4$ and calculating $\Phi 34$.

ln I3 and ln I4 were measured at given time intervals, and the results were plotted on a graph of FIG. 4 where the abscissa represents ln I4 and the ordinate ln I3.

These points are processed by the method of least squares, to thereby form a regression line b. If the light-absorbing material concentration Cd is fixed, a point obtained by the measurement goes and returns along the regression line every one pulsation. An inclination of the regression line is given by $\Delta \ln I3/\Delta \ln I4$. Then, the light-absorbing material concentration Cd can be obtained when the equation (12) is calculated using the inclination of the regression line.

Figure 5:
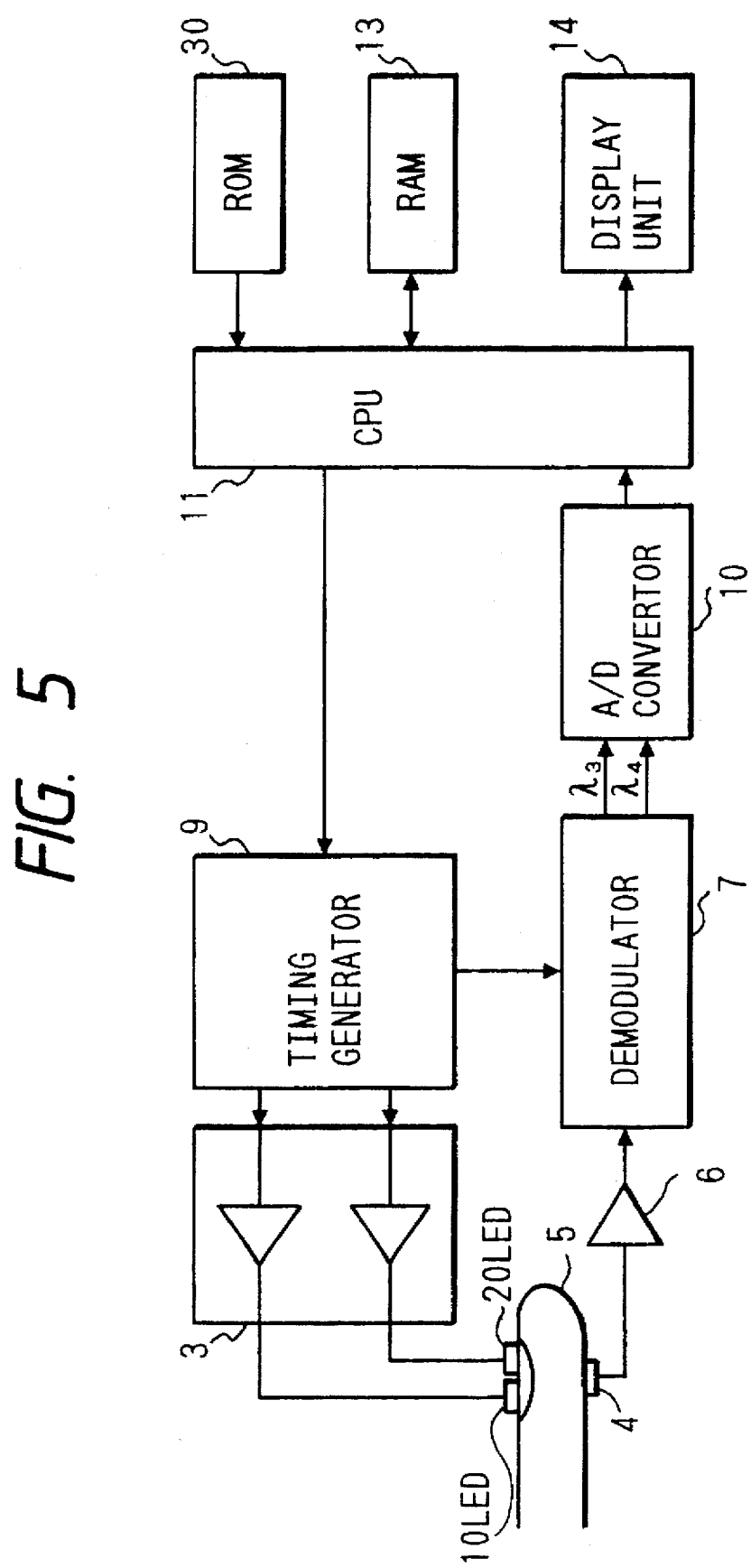
FIG. 5 is a block diagram showing an overall arrangement of seocnd embodiment of the present invention.

A specific example of the apparatus for measuring the concentration of light-absorbing materials in blood, designed on the basis of the above-mentioned principle, will be described. FIG. 5 is a block diagram showing an overall arrangement of an apparatus for measuring the concentration of light-absorbing materials in blood according to a second embodiment of the present invention.

In FIG. 5, like or equivalent portions are designated by like reference numerals in FIG. 1, for simplicity of explanation. A LED 10 emits light of wavelength $\lambda 3$, and a LED20 emits light of wavelength $\lambda 4$. A ROM 30 stores a program described in a flowchart shown in FIG. 6.

The operation of the apparatus for measuring the concentration of light-absorbing materials in blood, which is constructed as mentioned above, will be described with reference to FIG. 6 showing a flowchart.

Steps 201 to 203 are the same as the steps 101 to 103 in the flowchart shown in FIG. 3. No further description of them will be given here.

The CPU 11 computes a light-absorbing material concentration Cd by using the equation (12) and an inclination calculated in the step 203 (step 204).

The results of the computing process are displayed by the display device 14 and/or recorded by a recorder, not shown.

THIRD EMBODIMENT

The third embodiment of the invention will be described.

The invention is applied to the form of an apparatus for measuring a dye dilution curve. The principle of the invention will first be described.

A blood absorbance Ab of light transmitted through blood containing dye, as described above, is given by the following equation $$Ab = \{(Eh + EdCd/Hb)(Eh + EdCd/Hb + F)\}^{1/2} \cdot Hb \cdot D \quad (13)$$

The dye contained is ICG (indocyanine - green). Two wavelengths $\lambda 5$ and $\lambda 6$ are used, and suffixes 5 and 6 indicate the wavelengths having the following values.

$\lambda 5 = 805$ nm. At this wavelength, the absorbance of ICG is peaked, and the light absorbing coefficient of hemoglobin is constant irrespective of the oxygen saturation.

$\lambda 6 = 890$ nm. At this wavelength, the absorbance of ICG is negligible, and the light absorbing coefficient of hemoglobin is substantially constant irrespective of the oxygen saturation. For the wavelengths $\lambda 5$ and $\lambda 6$, the equation (13) can be rewritten by $$Ab5 = \{(Eo5 + Ed5Cd/Hb)(Eo5 + Ed5Cd/Hb + F)\}^{1/2} \cdot Hb \cdot D \quad (14)$$

$$Ab6 = \{Eo6(Eo6 + F)\}^{1/2} \cdot Hb \cdot D \quad (15)$$

where Eo5 and Eo6 are light absorbing coefficients of oxyhemoglobin at the wavelengths $\lambda 5$ and $\lambda 6$. A ratio of the measured Ab5 and Ab6 is expressed by $$\Psi = Ab5/Ab6 \quad (16)$$
$$= \{(Eo5 + Ed5Cd/Hb)(Eo5 + Ed5Cd/Hb + F)\}^{1/2}/$$
$$\{Eo6(Eo6 + F)\}^{1/2}$$

The hemoglobin concentration Hb of a subject is measured.

In the equation (16), only Cd is unknown. From this equation, Cd is given as the root of the quadratic equation. The absorbancies Ab5 and Ab6 can be calculated by the following equations $$Ab5 = \ln I05 - \ln I5 \quad (17)$$

$$Ab6 = \ln I06 - \ln I6 \quad (18)$$

where I5 and I6: intensities of the transmitted light when blood is present in the tissue; and I05 and I06: intensities of the transmitted light when blood is absent in the tissue.

How to determine the intensities of the transmitted light when blood is absent in the tissue, ln I05 and ln I06, will be described.

Blood in the tissue is pulsating. When the arterial blood is equal to the venous blood in the optical density of the blood (absorbance/thickness of the blood), viz., the arterial blood is equal to the venous blood in the light absorbing coefficient of the hemoglobin and in the concentration of dye in blood, a ratio of a blood absorbance $\Delta Ab$ of the blood pulsation component in the whole blood absorbance Ab is invariable at the wavelengths $\lambda 5$ and $\lambda 6$, and is given by $$\Delta Ab5/\Delta Ab6 = Ab5/Ab6 \quad (19)$$

Hence, the equation (16) can be rewritten into $$\Psi = \Delta Ab5/\Delta Ab6 \quad (20)$$
$$= \Delta \ln I5/\Delta \ln I6$$
$$= \{(Eo5 + Ed5Cd/Hb)(Eo5 + Ed5Cd/Hb + F)\}^{1/2}/$$
$$\{Eo6(Eo6 + F)\}^{1/2}$$

Light intensities ln I5 and ln I6 are plotted as points on the coordinates of which the ordinate represents ln I5, and the abscissa represents ln I6. When the light-absorbing material concentration Cd is invariable, the transmitted light is varied by only the influence of a variation of the thickness of the blood, which is caused by the pulsation. Therefore, these points are linearly arrayed on the coordinates.

These points are processed to form the regression line. The line, when extended, passes through the bloodless level point (ln I05, ln I06).

Figure 7:
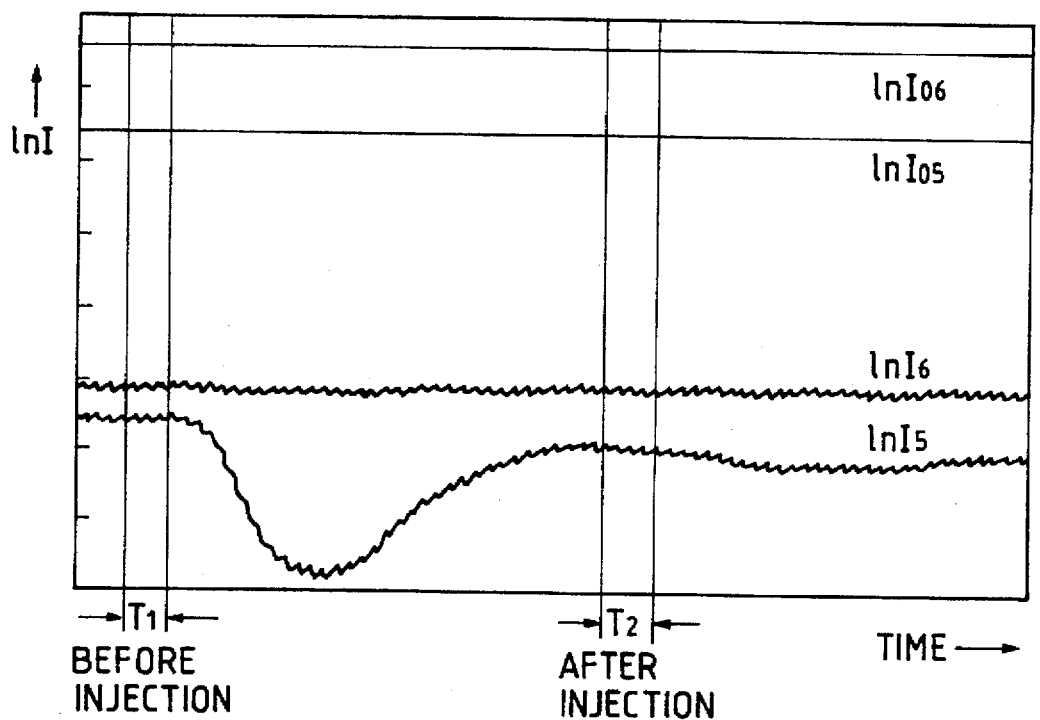
FIG. 7 is a graph useful in explaining the operation of a third embodiment of the present invention.

As shown in FIG. 7, during two stable periods T1 and T2 of different dye concentrations, two straight lines passing the bloodless level points are obtained when measuring values ln I5 and ln I6 are gained at a plural number of time points.

Figure 8:
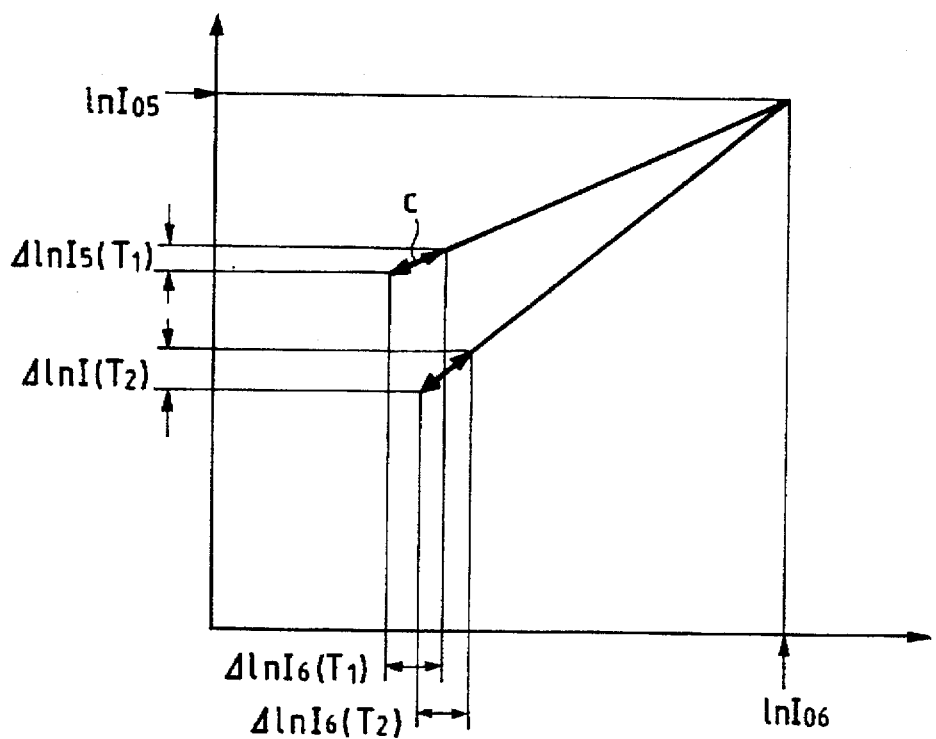
FIG. 8 is a graph useful in explaining the operation of the third embodiment of the present invention.

As shown in FIG. 8, the bloodless level points are obtained by extending these straight lines, and hence bloodless levels ln I05 and ln I06 are obtained.

By obtaining the bloodless levels ln I05 and ln I06, a momentarily varying $\Psi$ is obtained by the equations (16) to (18), and Cd varying with the variation of $\Psi$ can be obtained, and as a result, a dye dilution curve can be depicted.

Before dye is injected into a living body, the concentration of dye in blood is kept at zero for a sufficiently long time. Because of this, the regression line of each beat of the pulsation is invariable. Therefore, formation of the regression line of a number of beats will improve a reliability of the resultant regression line.

In forming the second regression line, there is no need of limiting the number of beat for forming the regression line to one beat.

A specific example of the apparatus for measuring a dye dilution curve, designed on the basis of the above-mentioned principle, will be described.

Figure 9:
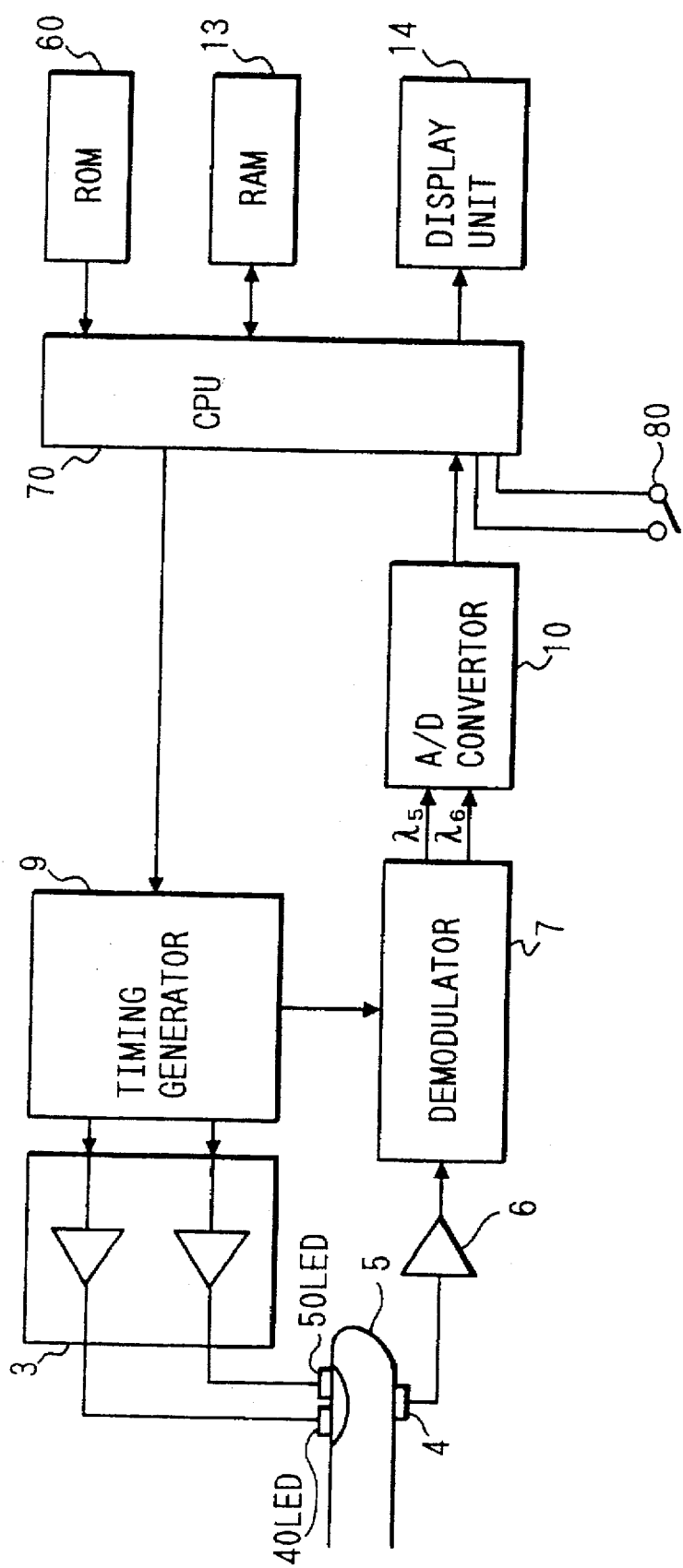
FIG. 9 is a block diagram showing an overall arrangement of the third embodiment of the present invention.

FIG. 9 is a block diagram showing an overall arrangement of the apparatus for measuring a dye dilution curve according to a second embodiment of the present invention.

Figure 10:
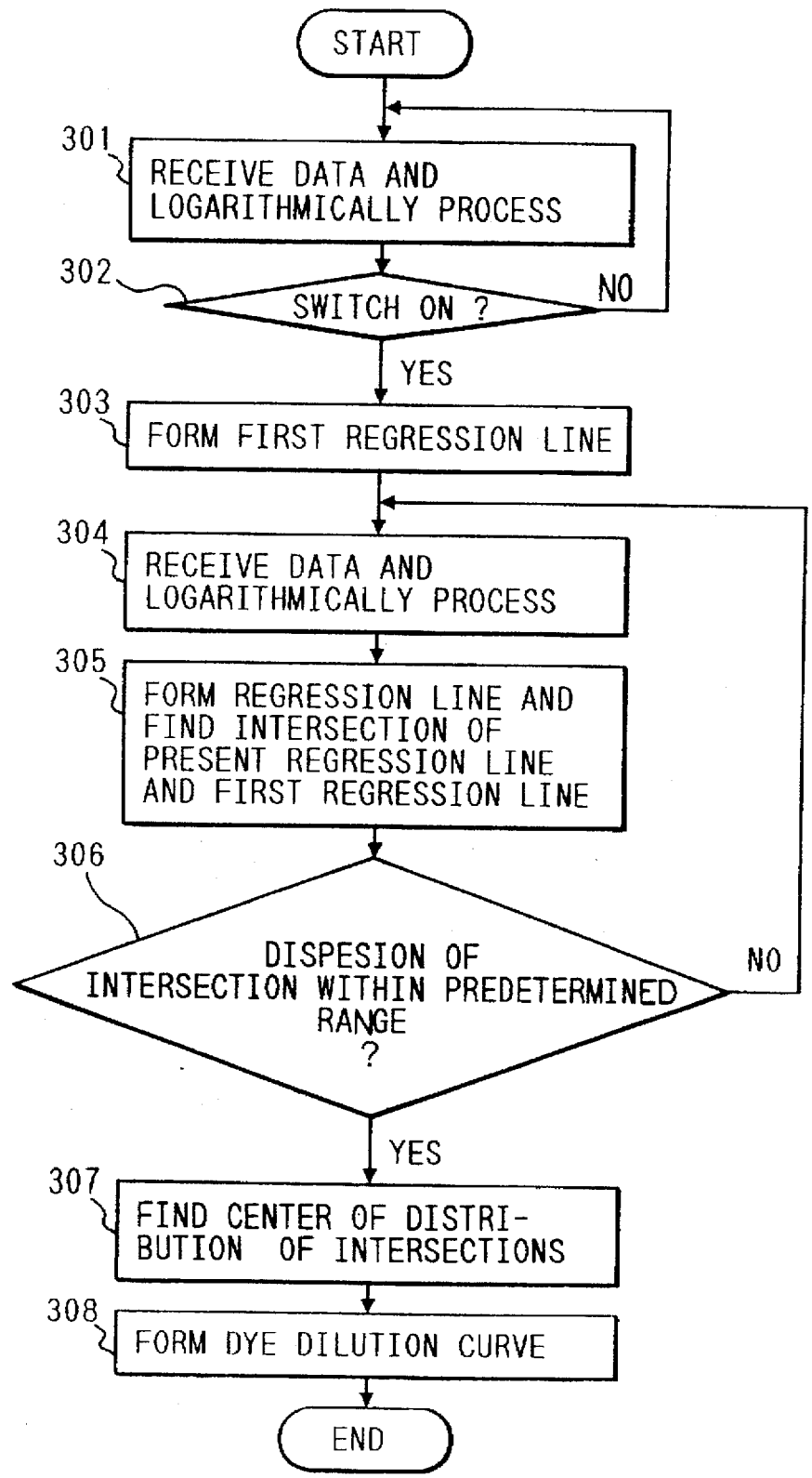
FIG. 10 is a flowchart in explaining the operation of the third embodiment of the present invention.

In FIG. 9, like or equivalent portions are designated by like reference numerals in FIG. 1, for simplicity of explanation. Major difference of the apparatus of the present embodiment from FIG. 1 apparatus are: a LED40 emits light of wavelength $\lambda 5$, a LED50 emits light of wavelength $\lambda 6$, and a program stored in a ROM 60 is as shown in FIG. 10. An additional difference is a switch 80, connected to a CPU 70, for showing dye injection.

The operation of the apparatus for measuring a dye dilution curve thus constructed will be described with reference to FIG. 10.

As a first step, the CPU 70 fetches data I5 and I6, which are derived from the A/D converter 10, logarithmically processes the fetched data, and stores the resultant data (step 301).

This operation continues till an operator injects dye into a subject and turns on the switch 80.

The CPU 70 recognizes the turn-on of the switch 80 (step 302), and forms a first regression line c (before dye injection) shown in FIG. 8 using the data stored in the step 301 (step 303). The CPU 70 fetches data I5 and I6, which are derived from the A/D converter 10, for a preset time (e.g., about 10 beats of the pulsation), logarithmically processes the data (step 304), forms a regression line using the data, and finally finds an intersection of the present regression line and the first regression line (step 305).

The CPU 70 determines whether or not the number of the intersections is increased to reach a preset number of intersections, and a dispersion of the intersections is within a predetermined range (step 306). If the answer is NO, the CPU 70 returns to the step 304, and if it is YES, the CPU advances to a step 307.

In the step 307, the CPU 70 finds a center of the distribution of intersections (step 307). This point is a bloodless level point (lnI05, lnI06).

Figure 11:
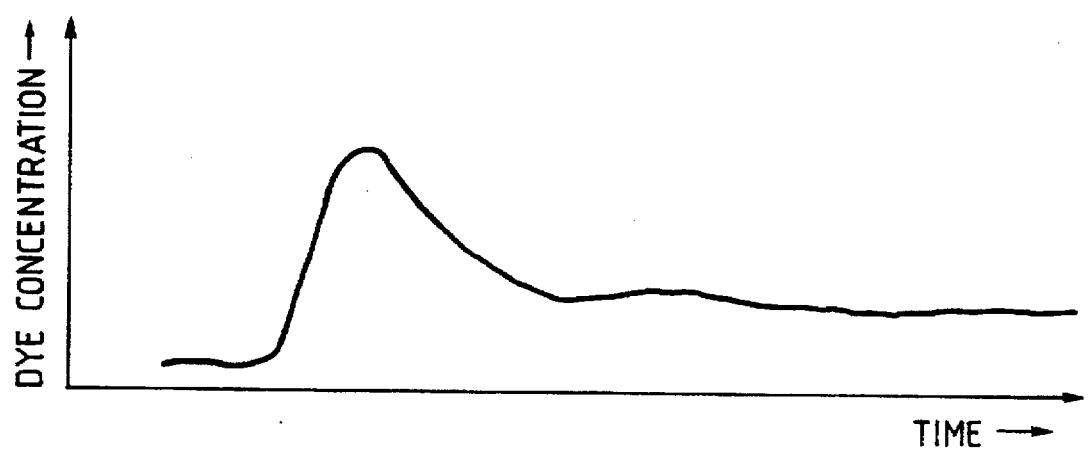
FIG. 11 is a graphs showing the results of a measurement of the third embodiment of the present invention.

The CPU 70 forms a dye dilution curve as shown in FIG. 11, using all the data fetched in the step 304, the bloodless level point (lnI05, lnI06), and the equations (16) to (18).

The present embodiment detects the bloodless level in a real time manner, to thereby reduce time taken from a measurement start to detection of the bloodless level. The embodiment detects a bloodless level by one-time dye injection, and forms a dye dilution curve. The embodiment may be modified such that at the first dye injection, only the bloodless level is detected, and at the second dye injection a dye dilution curve is formed using the bloodless level previously detected, in a real time manner.

In the present embodiment, a number of regression lines are formed and a bloodless level is calculated on the basis of the regression lines. Alternatively, regression lines are formed during two periods where the dye concentration is satisfactorily stable as shown in FIG. 7, and their intersections are detected. In the alternative, an exact bloodless level is secured by only two regression lines.

According to the present invention, the present invention provides an apparatus for measuring oxygen saturation in blood, which is high in measurement accuracy.

According to the present invention, the present invention provides an apparatus for measuring a dye dilution curve, which is high in measurement accuracy and low in power consumption.

What is claimed is:

1. An apparatus for measuring the concentration of light-absorbing materials in blood comprising:

light generating means for projecting light beams of two different wavelengths to a living body;

photo sensing means for receiving light beams transmitted through the living body and for converting received light beams into electrical signals;

regression line computing means for forming at least two regression lines for at least two periods, using values, at a plurality of time points, of said electrical signals output from said photo sensing means, wherein coordinates of points on said at least two regression lines refer to an ordinate and an abscissa which represent the magnitudes of said electrical signals;

bloodless level computing means for computing a bloodless level of said received light beams using intersections of extensions of said at least two regression lines;

absorbance calculating means for computing a blood absorbance of said received light beams of different wavelengths by using said bloodless level computed by said bloodless level computing means and said electrical signals; and concentration computing means for computing the concentration of light absorbing materials in blood using said absorbance computed by said absorbance calculating means.

2. The apparatus as claimed in claim 1, wherein said bloodless level computing means is arranged to successively detect intersections of said at least two regression lines, one of said at least two regression lines being obtained during a period before dye injection, and the other of said at least two regression lines being obtained during period after dye injection, and when a dispersion of said intersections is determined to be within a predetermined range, said bloodless level computing means determines that a center of the distribution of said intersections represents a bloodless level.

3. A method for measuring the concentration of light-absorbing materials in blood comprising the steps of:

projecting light beams of two different wavelengths to a living body;

receiving light beams transmitted through the living body and converting received light beams into electrical signals;

forming at least two regression lines for at least two periods, using values, at a plurality of time points, of said electrical signals output from a photo sensing means, where coordinates of points on said at least two regression lines include a value of an ordinate and an abscissa representing the magnitudes of said electrical signals;

calculating a bloodless level of said received light beams using intersections of extensions of said at least two regression lines obtained by a regression line computing means;

calculating a blood absorbance of said received light beams of different wavelengths by using said bloodless level computed by a bloodless level computing means and said electrical signals output from said photo sensing means; and computing the concentration of light absorbing materials in blood using said blood absorbance.

4. The method as claimed in claim 3, wherein said step of calculating said bloodless level includes the steps of:

successively obtaining intersections of said at least two regression lines, one of said at least two regression lines being obtained during a period before dye injection, and the other of said at least two regression lines being obtained during period after dye injection; and determining the center of the distribution of intersections as representing a bloodless level when a dispersion of the intersections lies within a predetermined range.

\* \* \* \* \*